(12) United States Patent
Carelsen et al.

(10) Patent No.: US 9,795,357 B2
(45) Date of Patent: Oct. 24, 2017

(54) POSITIONING DISTANCE CONTROL FOR X-RAY IMAGING SYSTEMS

(71) Applicant: KONINKLIJKE PHILIPS N.V., Eindhoven (NL)

(72) Inventors: Bart Carelsen, Eindhoven (NL); Peter Belei, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 640 days.

(21) Appl. No.: 14/358,093

(22) PCT Filed: Nov. 7, 2012

(86) PCT No.: PCT/IB2012/056209
§ 371 (c)(1),
(2) Date: May 14, 2014

(87) PCT Pub. No.: WO2013/072810
PCT Pub. Date: May 23, 2013

(65) Prior Publication Data
US 2014/0314205 A1 Oct. 23, 2014

Related U.S. Application Data

(60) Provisional application No. 61/559,471, filed on Nov. 14, 2011.

(51) Int. Cl.
*A61B 6/00* (2006.01)
*A61B 6/10* (2006.01)
*A61B 5/11* (2006.01)

(52) U.S. Cl.
CPC ............ *A61B 6/547* (2013.01); *A61B 6/4458* (2013.01); *A61B 6/461* (2013.01); *A61B 5/1113* (2013.01);
(Continued)

(58) Field of Classification Search
CPC ...... A61B 5/1113; A61B 5/1126; A61B 6/102; A61B 6/4405; A61B 6/4441; A61B 6/461; A61B 6/547; A61B 6/4458
See application file for complete search history.

(56) References Cited

U.S. PATENT DOCUMENTS 4,578,757 A 3/1986 Stark
2003/0099328 A1 5/2003 Jensen et al.
(Continued)

FOREIGN PATENT DOCUMENTS

CN 1372870 A 10/2002
DE 10200534 A1 * 7/2003 ........... A61B 6/0407
(Continued)

OTHER PUBLICATIONS

Ladikos, Real-time Multi-view 3D Reconstruction for Interventional Environments, Mar. 11, 2011, Technische Universität München, Dissertation, 164 pages.*
(Continued)

*Primary Examiner* — Glen Kao

(57) ABSTRACT

The present invention relates to providing guiding information for operating an X-ray imaging system. In order to provide an improved positioning distance control facilitating the work flow, an X-ray imaging system (10) is provided, comprising a moveable X-ray source (12) and/or a moveable X-ray detector (14). The system further comprises a plurality of object-surface detecting sensors (16), a positioning detection arrangement (18), a processing unit (20), and a display unit (22). The sensors are arranged such to detect object data of objects located between the X-ray source and the X-ray detector. The positioning detection arrangement is provided to detect the current position of the X-ray source and/or the X-ray detector and the position of the sensors. The processing unit is configured to compute a situation-map (26) of the current spatial situation between the X-ray source and the
(Continued)

X-ray detector based on the object data provided by the sensors and the current position, the situation-map distinguishing at least between empty spaces and spaces occupied by rigid objects. The situation-map comprises a representation (25) of the X-ray source and the X-ray detector in relation to the spatial situation. Further, the display unit is configured to display the situation-map to a user operating the X-ray imaging system.

16 Claims, 5 Drawing Sheets

(52) U.S. Cl.
CPC ............ *A61B 5/1126* (2013.01); *A61B 6/102* (2013.01); *A61B 6/4405* (2013.01); *A61B 6/4441* (2013.01)

(56) References Cited

U.S. PATENT DOCUMENTS

| | | | |
|---|---|---|---|
| 2007/0086570 A1 | 4/2007 | Spahn | |
| 2007/0104309 A1 | 5/2007 | Schonborn et al. | |
| 2007/0211847 A1 | 9/2007 | Graumann et al. | |
| 2008/0031413 A1 | 2/2008 | Bouvier et al. | |
| 2008/0063250 A1 | 3/2008 | Ozawa | |
| 2008/0089467 A1 | 4/2008 | Lauritsch et al. | |
| 2008/0279333 A1* | 11/2008 | Sattler | A61B 6/102 378/98.2 |
| 2009/0022275 A1 | 1/2009 | Grebner et al. | |
| 2011/0001898 A1 | 1/2011 | Mikubo et al. | |
| 2011/0224904 A1 | 9/2011 | Feiten et al. | |

FOREIGN PATENT DOCUMENTS

| | | | | |
|---|---|---|---|---|
| DE | 102008046345 A1 | * | 3/2010 | ............ A61B 6/102 |
| DE | 102008046346 A1 | * | 3/2010 | ............ A61B 6/102 |
| DE | 102008046348 A1 | * | 3/2010 | ............ A61B 6/102 |
| DE | 102008046344 B4 | * | 6/2010 | ............ A61B 6/102 |
| FR | 2880790 A1 | | 7/2006 | |
| JP | 2005013489 A | | 1/2005 | |
| JP | 2006051403 A | | 2/2006 | |
| JP | 2009022602 A | | 2/2009 | |

OTHER PUBLICATIONS

Bott et al., Informatics in Radiology: Use of a C-Arm fluoroscopy Simulator to Support Training in Intraoperative Radiology, May 2011, RadioGraphics, vol. 31, pp. E65-E76.*

Ladikos et al., Real-time 3D Reconstruction for Collision Avoidance in Interventional Environments, 2008, MICCAI 2008, Part II, LNCS 5242, pp. 526-534.*

Ladikos et al., https://static-content.springer.com/esm/chp%3A10.1007%2F978-3-540-85990-1_63/MediaObjects/978-3-540-85990-1_63_MOESM1_ESM.avi.*

PTO English translation of Feiten et al. (DE 10 2008 046 345 A1).*

PTO 115346 which is an English translation of Soukal (DE 102 00 534 A1).*

* cited by examiner

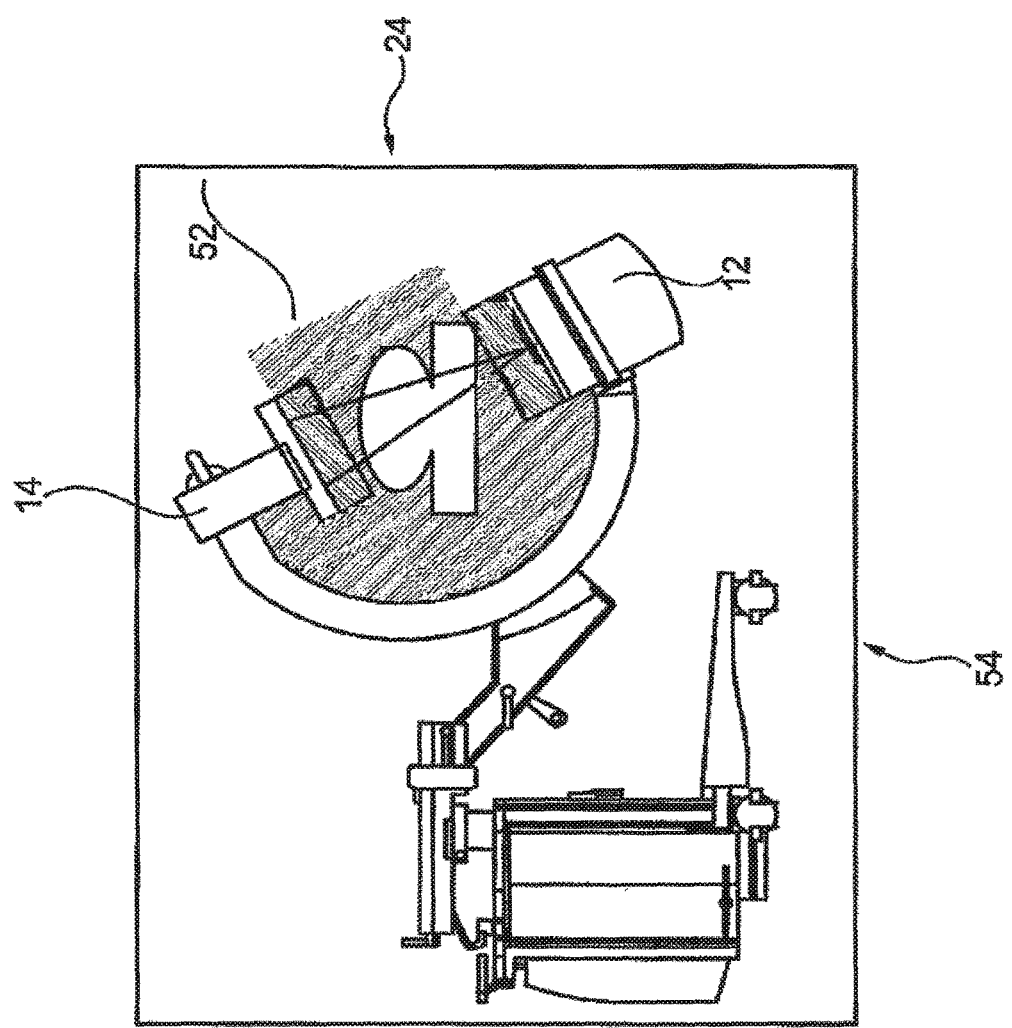

POSITIONING DISTANCE CONTROL FOR X-RAY IMAGING SYSTEMS

This application is a national stage application under 35 U.S.C. §371 of International Application No. PCT/IB2012/056209 filed on Nov. 7, 2012 and published in the English language on May 23, 2013 as International Publication No. WO/2013/072810, which claims priority to U.S. Application No. 61/559,471 filed on Nov. 14, 2011, the entire disclosures of which are incorporated herein by reference.

FIELD OF THE INVENTION

The present invention relates to an X-ray imaging system, a method for providing guiding information for operating an X-ray imaging system, a computer program element and a computer readable medium.

BACKGROUND OF THE INVENTION

For X-ray imaging, the X-ray source and the X-ray detector have to be positioned in relation to the patient. For example, for moveable X-ray systems, positioning is an important issue in terms of image quality and handling. For positioning, also possible collisions with other equipment or the patient must be avoided. For example, U.S. Pat. No. 4,578,757 describes a device for prevention of collision between a patient table and an X-ray imaging system in form of a movable C-arm. However, estimating and assessing an optimal view is time and X-ray dose consuming. It has been shown further that avoiding collisions is an important process, but requires time and often leads to a change of projection.

SUMMARY OF THE INVENTION

Thus, there may be a need to provide an improved positioning distance control facilitating the work flow.

The object of the present invention is solved by the subject-matter of the independent claims, wherein further embodiments are incorporated in the dependent claims.

It should be noted that the following described aspects of the invention apply also for the X-ray imaging system, the method for providing guiding information for operating an X-ray imaging system, the computer program element and the computer readable medium.

According to a first aspect of the present invention, an X-ray imaging system is provided, comprising a moveable X-ray source and/or a moveable X-ray detector. The X-ray imaging system further comprises a plurality of object-surface detecting sensors, a positioning detection arrangement, a processing unit, and a display unit. The sensors are arranged such to detect object data of objects located between the X-ray source and the X-ray detector. The positioning detection arrangement is provided to detect the current position of the X-ray source and/or the X-ray detector and the position of the sensors. The processing unit is configured to compute a situation-map of the current spatial situation between the X-ray source and the X-ray detector based on the object data provided by the sensors and the current position. The situation-map distinguishes at least between empty spaces and spaces occupied by rigid objects. The situation-map comprises a representation of the X-ray source and the X-ray detector in relation to the spatial situation. The display unit is configured to display the situation-map to a user operating the X-ray imaging system.

According to the present invention, the term "rigid objects" relates to objects such as a patient table, a patient, interventional equipment, and the like. The term "interventional" also relates to "surgical", for instance interventional equipment also comprises surgical equipment.

The sensors are configured to detect objects behind flexible draping, such as cloth draping.

The sensors may also be configured to detect surfaces of the flexible draping. The sensors may also be provided with adaptable sensitivities, i.e. different sensitivities.

The situation-map may be provided with a colour-coding, wherein different colours represent different types of space, e.g. empty space, space occupied by rigid objects, and space occupied by flexible draping. For example, the colours on the display indicate different distance regions of the X-ray imaging system to the object, e.g. red=collision or close, yellow=critical, green=safe.

According to an exemplary embodiment, the object-surface detecting sensors are provided as ultrasound sensors.

The object-surface detecting sensors may also be provided as capacitive sensors or induction sensors.

According to an exemplary embodiment, the sensors provide surface data of a number of spatial segments. The processing unit is configured to combine the surface data of the spatial segments to form a topogram of the current spatial situation.

For example, the topogram is a position diagram, for example showing a cross-sectional image. The surface data provided by the sensors may comprise topographic information, and the processing unit is configured it add the topographic information to form the topogram.

For example, the positioning detector arrangement provides an encoder function to show the situation-map in a context, i.e. fixed frame of reference.

According to an exemplary embodiment, the situation-map comprises a visual representation of the X-ray source and the X-ray detector in their current position.

According to an exemplary embodiment, the current spatial situation in the situation-map is provided in relation to a spatial frame of reference.

According to an exemplary embodiment, the processing unit is configured to indicate, in the situation-map, a geometrical form of an X-ray beam to be radiated from the X-ray source to the X-ray detector. The situation-map is a positioning guide for the operator of the X-ray imaging system.

The X-ray beam may be indicated for the current position of the X-ray source and the X-ray detector. The processing unit may also be configured to indicate an area of reconstruction for X-ray acquisition from a number of positions along an arc-like trajectory.

According to an exemplary embodiment, the X-ray imaging system is a C-arm imaging system comprising a C-arm structure, wherein the X-ray source and the X-ray detector are mounted to opposing ends of a C-arm. The sensors are mounted to the C-arm structure in a distributed manner along the inner side of the arc. The positioning detection arrangement comprises angulation detectors for providing information about the movement of the C-arm.

For example, the sensors coincide with the moving field of the C-arm, e.g. they are mounted on a detector or source housing.

According to an exemplary embodiment, the processing unit is configured to compute a simulation of at least one movement of the X-ray source and the X-ray detector, and the display unit is configured to display the at least one resulting simulated spatial situation.

According to a second aspect of the present invention, a method for providing guiding information for operating an X-ray imaging system is provided, comprising the following steps:

a) detecting object data of objects located between a moveable X-ray source and a moveable X-ray detector with a plurality of object-surface detecting sensors;
b) detecting current position of the X-ray source and the X-ray detector and the position of the sensors with a positioning detection arrangement;
c) computing a situation-map of a current spatial situation between the X-ray source and the X-ray detector based on the object data and the current position; and
d) displaying the situation-map on a display to a user operating the X-ray imaging system.

The situation-map is distinguishing at least between empty spaces and spaces occupied by rigid objects. The situation-map comprises a representation of the X-ray source and the X-ray detector in relation to the spatial situation.

According to an aspect of the present invention, an operator of an X-ray imaging system, for example a C-arm system, is provided with a topogram. The topogram is generated by adding signals from a number of sensors, for example ultrasound sensors, thus providing information about the spatial situation in real-time. By providing ultrasound sensors being able to "see through" draping, additional room for movement may be detected, which would otherwise be not used, since it is hidden behind the draping, and thus not visible for the user. As a further option, a simulation of an X-ray beam shape is also provided in combination with a situation-map, thus supporting the operator of the X-ray imaging system in guiding and positioning.

According to an aspect of the present invention, an operator is provided with a direct visible feedback in form of the situation-map. Thus, an operator can work in "the blind" as the C-arm "disappears" in the draping. However, the present invention provides the necessary information for a facilitated and precise positioning of the imaging system, avoiding collisions.

According to a further aspect, the C-arc's angulation is tracked with any kind of electronic sensors. The inside of the C-arc is covered with a number of ultrasound detectors, for example piezoelectric detectors, in order to map the inside, which detectors need to see through the normal draping. The visual display displays both angulations as well as a map of the inside of the C-arc. Preferably, colours are used to distinguish empty space, occupied space by a patient, and areas where the C-arc hits or approximates the contours of the patient or patient's bed.

These and other aspects of the invention will become apparent from and be elucidated with reference to the embodiments described hereinafter.

BRIEF DESCRIPTION OF THE DRAWINGS

Exemplary embodiments of the invention will be described in the following with reference to the following drawings.

FIG. 3 shows an exemplary embodiment of a positioning guide according to the present invention.

DETAILED DESCRIPTION OF EMBODIMENTS

Figure 1:
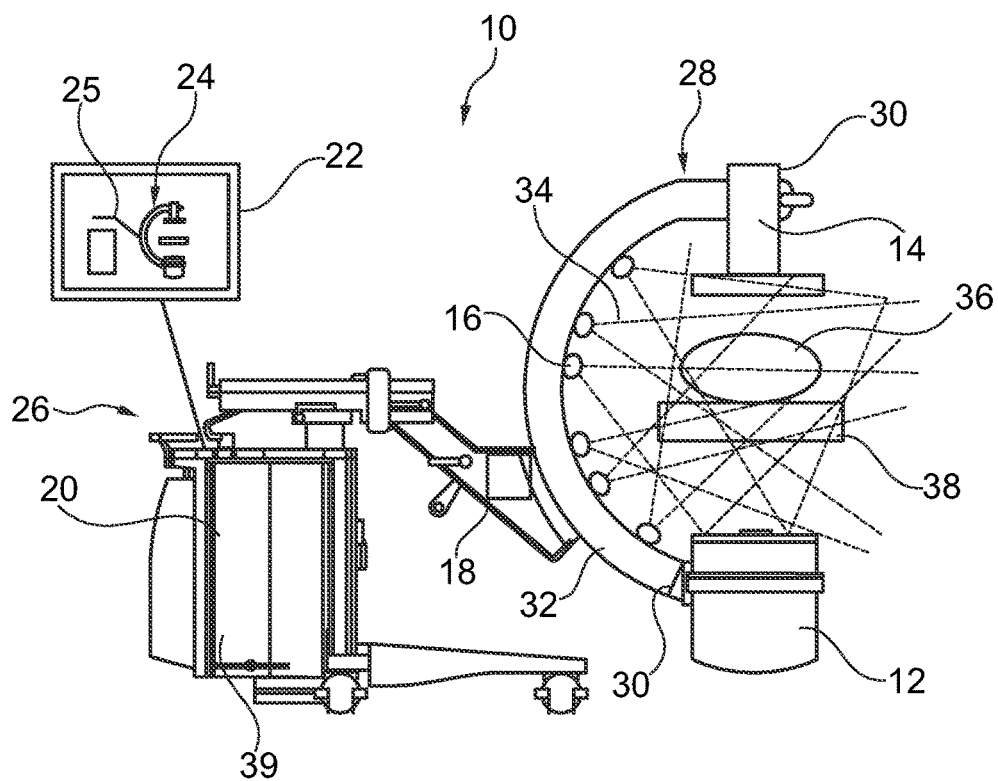
FIG. 1 shows an exemplary embodiment of an X-ray imaging system according to the present invention.

FIG. 1 shows an X-ray imaging system 10 comprising a moveable X-ray source 12 and a moveable X-ray detector 14. Further, a plurality of object-surface detecting sensors 16 is provided. Still further, a positioning detection arrangement 18, a processing unit 20, and a display unit 22 are provided.

The sensors 16 are arranged such to detect object data of objects located between the X-ray source and the X-ray detector. The positioning detection arrangement 18 is provided to detect the current position of the X-ray source 12 and the X-ray detector 14 and the position of the sensors 16.

The processing unit 20 is configured to compute a situation-map 24 of the current spatial situation between the X-ray source and the X-ray detector based on the object data provided by the sensors 16 and the current position. The situation-map 24 is distinguishing at least between empty spaces and spaces occupied by rigid objects. The situation-map 24 is further described with reference to FIGS. 2A to 2C. The situation-map 24 comprises a representation 25 of the X-ray source 12 and the X-ray detector 14 in relation to the spatial situation. The display unit 22 is configured to display the situation-map 24 to a user operating the X-ray imaging system.

The X-ray imaging system 10 is shown as a C-arm imaging system 26, comprising a C-arm structure 28. The X-ray source 12 and the X-ray detector 14 are mounted to opposing ends 30 of a C-arm 32. The sensors 16 are mounted to the C-arm structure 28 in a distributed manner along the inner side of the arc. The positioning detection arrangement 18 comprises angulation detectors for providing information about the movement of the C-arm.

The object-surface detecting sensors 16 are provided as ultrasound sensors. For example, the sensors are configured to detect objects behind flexible draping. They may also be configured to detect surfaces of flexible draping. As a further option, they may be provided with adaptable sensitivities. The sensors coincide with the moving field of the C-arm, e.g. they are mounted on the detector or source housing according to a further example.

The plurality of sensors 16 is provided such that the field of the moving range is sufficiently covered. For example, the plurality of sensors 16 is provided such that the viewing angles of the sensors at least partly overlap. This is indicated in FIG. 1 with a viewing angle 34 for a number of the sensors 16.

FIG. 1 also schematically shows a patient 36 and a patient table 38.

It must be noted that the present invention is also provided for other X-ray imaging systems, wherein the source and/or the detector are movable, for example an X-ray system with robotic arms instead of the C-arm, to which robotic arms the X-ray source and the X-ray detector are mounted respectively.

It is further noted that the C-arm imaging system 26 in FIG. 1 is a portable system, wherein the C-arm is mounted to a support allowing movement of the C-arm, wherein the support is mounted to a moveable base 39.

However, the C-arm system can also be a stationary system in which the C-arm is mounted to a support allowing movement of the C-arm, wherein the support is fixedly mounted to a building's structure.

Figure 2A:
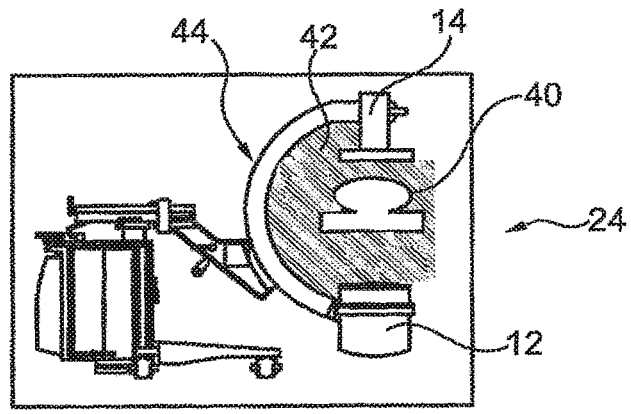
FIGS. 2A to 2C show different examples of a situation-map being displayed on a display according to the present invention.
Figure 2B:
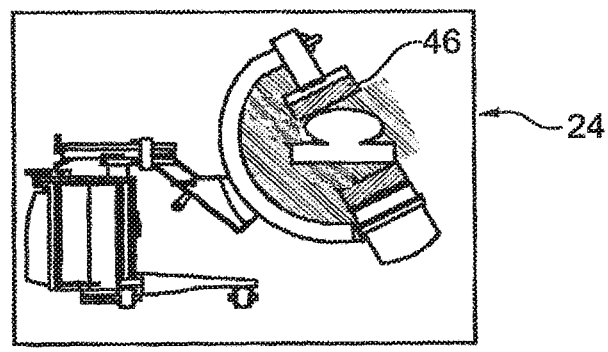
Figure 2C:
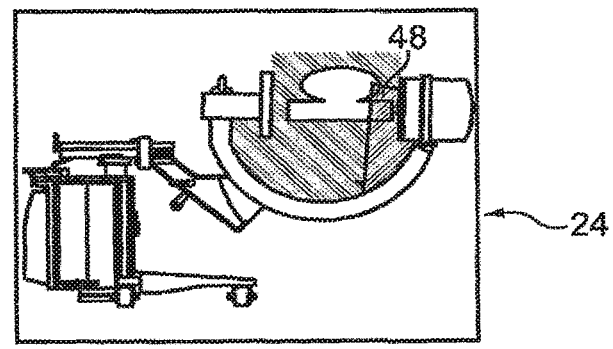

FIGS. 2A to 2C show different examples for the situation map 24 shown on the display unit 22.

As indicated above, the sensors 16 provide surface data of a number of spatial segments, which is combined to form a topogram of the current spatial situation. For example, the topogram is a position diagram, for example showing a cross-sectional image.

In FIG. 2A, the situation-map 24 is shown for a first position of the C-arm. An object 40, for example the patient arranged on the patient table, is shown in a first graphical coding, for example in a colour-coding. Thus, the object 40 represents a rigid structure. Around the rigid structure, an empty space 42 is indicated with a second graphical pattern. Further, the X-ray source 12 and the X-ray detector 14 are shown with a C-arm structure 44.

FIG. 2B shows a further example of the situation-map 24, in which the C-arm has been rotated counter-clockwise. In the respective position, a critical situation has been determined for the X-ray source and the X-ray detector 12, 14, which critical situation is indicated with a first hashed pattern 46.

FIG. 2C shows a further example for the situation-map 24, in which the C-arm has been rotated further counter-clockwise. A collision is determined for the respective position, indicated with second dashed pattern 48.

According to an exemplary embodiment, the situation-maps 24 of FIGS. 2B and 2C may result from a computed simulation of at least one movement of the X-ray source 12 and the X-ray detector 14. Thus, the display unit 22 displays the at least one resulting simulated spatial situation.

For example, the situation-maps 24 of FIGS. 2A to 2C can be shown subsequently, or in combination on a single monitor or display arrangement. For example, the current situation is shown in FIG. 2A, whereas the simulated situations of FIGS. 2B and 2C are shown in a smaller scale on the side of the current situation.

Thus, the situation-map 24 of FIG. 2B and the situation-map 24 of FIG. 2C is a predictive situation-map.

The situation-map comprises an indication of potential collision situations.

According to an example of the present invention, the positioning detection arrangement 18 provides an encoder function to show the situation-map 24 in a context, i.e. fixed frame of reference.

This can also be explained referring to FIGS. 2A to 2C. However, in the following, it is assumed that FIGS. 2A to 2C show three different states of rotation, and not the simulated situations as described above. By detecting the movement of the C-arm, it is also detected how the sensors have been moved. Thus, by providing a fixed frame of reference, the sensors, although detecting from a different position compared between the positions of FIGS. 2A and 2B, the signals thus provided can still be combined to form a representation of the spatial situation arranged in the same frame of reference, i.e. in the same spatial orientation with relation to the operational room, for example.

According to a further example, the processing unit is configured to indicate, in the situation-map 24, a geometrical form of an X-ray beam 52, as shown in FIG. 3, to be radiated from the X-ray source 12 to the X-ray detector 14. The situation-map is a positioning guide 54 for the operator of the X-ray imaging system.

Thus, the user is provided with information in a straight-forward manner that helps in positioning the X-ray source such that the desired image acquisition procedure can be performed.

Figure 4:
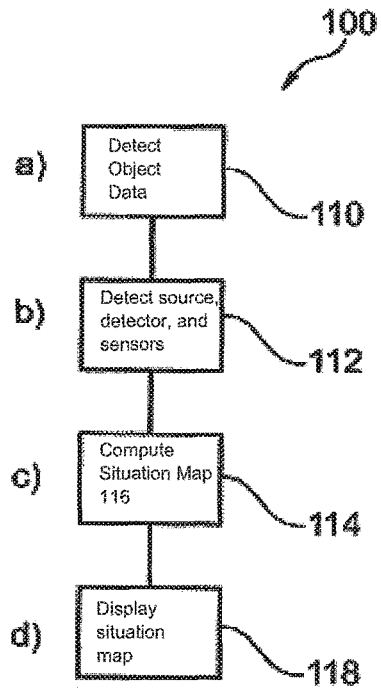
FIG. 4 shows basic steps of a method according to an exemplary embodiment of the present invention.

FIG. 4 shows a method 100 for providing guiding information for operating an X-ray imaging system. In a first detection step 110, object data of objects located between a moveable X-ray source and a moveable X-ray detector are detected with a plurality of object-surface detecting sensors. In a second detection step 112, current position of the X-ray source and the X-ray detector and the position of the sensors are detected with a positioning detection arrangement. Next, in a computing step 114, a situation-map 116 of a current spatial situation between the X-ray source and the X-ray detector is computed based on the object data and the current position. Further, in a display step 118, the situation-map is displayed on a display to a user operating the X-ray imaging system. The situation-map is distinguishing at least between empty spaces and spaces occupied by rigid objects. The situation-map further comprises a representation of the X-ray source and the X-ray detector in relation to the spatial situation.

The first detection step 110 is also referred to as step a), the second detection step 112 as step b), the computing step 114 as step c), and the displaying step 118 as step d).

Figure 5:
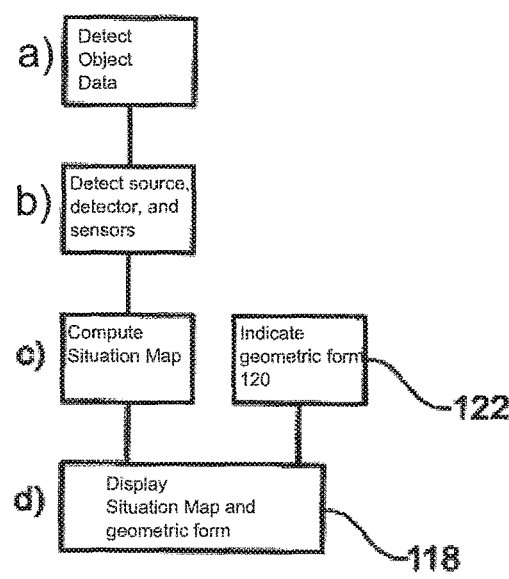
FIG. 5 shows a further example of a method according to the present invention.

As shown in FIG. 5, according to a further example, for step d), a geometrical form 120 of an X-ray beam to be radiated from the X-ray source to the X-ray detector is indicated in an indication step 122 in the situation-map as a positioning guide for the operator of the X-ray imaging system.

Figure 6:
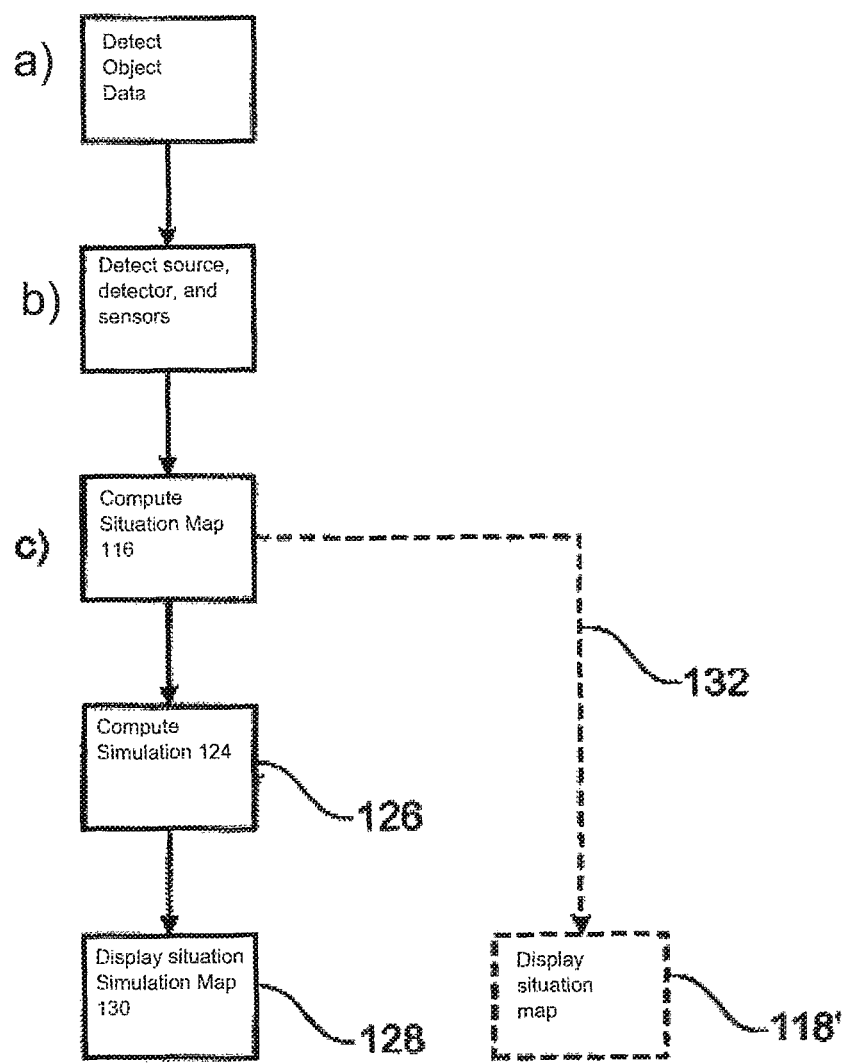
FIG. 6 shows a still further example of a method according to the present invention.

As shown in FIG. 6, according to a further example, a simulation 124 of at least one movement of the X-ray source and the X-ray detector is computed in a computing step 126, based on the computed situation map. According to a further example, this computational step 126 is based on at least steps a) and b). The at least one resulting simulated spatial situation is displayed in a display step 128 as situation simulation-map 130.

As also indicated in FIG. 6, the situation-map 116 may also be displayed in a further display step 118', the situation-map provided from step c), as indicated with dashed arrow 132.

According to a further example, a topogram is provided in real-time, also allowing the detection of space behind draping, for example, since the ultrasound sensors according to the present invention are adapted to such sensitivity that they can see through draping. For example, the object-surface detecting sensors allow setting a workable sensitivity. By providing the C-arm with an encoder function, a context is provided such that, although the C-arm may rotate, the topogram does not rotate on the display, but rather stays in the same spatial relation to the fixed frame of reference, for example a frame of reference of the operational room. The attachment of sensors 16 to the C-arm can be used in particular for mobile C-arm systems, where a calibration to an interventional room frame of reference is not necessary, since the mobile C-arm structure represents its own frame of reference.

For example, angulation sensors of the C-arc are provided to track the C-arc's angulation with certain accuracy as an input for the visual display. This is advantageous since angulation is the most performed movement of the C-arc during the procedure. Further, the C-arc's angulation is an important factor to understanding of C-arc with respect to patient anatomy. By providing this information in relation to the ultrasound detected surface (patient and table), thus allowing an encoding function, a situation-map is displayed in an intuitively manner. It is further advantageously in that with mobile C-arm angulation as an eccentric movement, the positioning is rather difficult. However, based on the situation-map according to the present invention, the positioning of mobile C-arms is facilitated. The angulation can be tracked in many ways, for example by accelerometers, potentiometers and the like.

According to a further example, the ultrasound echo sensors mounted on the C-arc to cover the area within the C of the C-arc provide a solution suitable in particular for mobile C-arm systems. Since the ultrasound echo sensors can work with different sensitivities, it is possible to see through the drapes. The mounting of the sensors allows a rigid fixation to a well-known shape, thus resulting in a high definition image of the area inside the C-arc.

In convex shapes, lots of overlaps of viewing angles of the sensors are provided to better define structures within reach, calibration, etc. To distinguish between solid bodies and (for example ECG) wires or other small but dense objects, the overlapping is provided.

The situation-map according to the present invention allows a quick visual feedback to the user. Further, by providing the above-mentioned simulation of an X-ray beam, the final positioning is provided without the need to use any extra X-ray dose. Rather, the positioning with respect to the patient, or the patient table, is provided without X-ray at all.

As a further option, the display is used to make multi-axis movements to mimic isocentric angulation. For example, the user can choose a point on a display image, which shows a map of the inside of the C-arc, around which point the C-arc moves iso-centrically by simultaneously moving laterally and vertically. Thus, even for such complex rotational movements, for example also for other forms of trajectories, the positioning can be adjusted without using X-ray radiation, but with rather only relying on the data provided by the plurality of sensors.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An X-ray imaging system, comprising:
a moveable X-ray source and a moveable X-ray detector;
a plurality of object-surface detecting sensors;
a positioning detection arrangement;
a processing unit; and
a display unit;
wherein the sensors are arranged such to detect object data of objects located between the X-ray source and the X-ray detector;
wherein the positioning detection arrangement is provided to detect the current position of the X-ray source and the X-ray detector and the position of the sensors;
wherein the processing unit is configured to compute a situation-map of the current spatial situation of a positional arrangement exclusively between the X-ray source and the X-ray detector based on the object data provided by the sensors and the current position, the situation-map distinguishing at least between empty spaces and spaces occupied by rigid objects; and
wherein the situation-map comprises a representation of the X-ray source and the X-ray detector in relation to the positioning detection arrangement;
wherein the display unit is configured to display the situation-map to a user operating the X-ray imaging system;
wherein the X-ray imaging system is a C-arm imaging system comprising a C-arm structure, wherein the X-ray source and the X-ray detector are mounted to opposing ends of a C-arm;
wherein the sensors are mounted to the C-arm structure in a distributed manner along an inner side of the arc; and
wherein the positioning detection arrangement comprises angulation detectors for providing information about the movement of the C-arm.

2. The X-ray imaging system according to claim 1, wherein the object-surface detecting sensors are provided as ultrasound sensors.

3. The X-ray imaging system according to claim 1, wherein the sensors provide surface data of a number of spatial segments; and
wherein the processing unit is configured to combine the surface data of the spatial segments to form a topogram of the current spatial situation.

4. The X-ray imaging system according to one of the preceding claims, wherein the situation-map comprises a visual representation of the X-ray source and the X-ray detector in their current position.

5. The X-ray imaging system according to claim 1, wherein the current spatial situation in the situation-map is provided in relation to a spatial frame of reference.

6. The X-ray imaging system according to claim 1, wherein the processing unit is configured to indicate, in the situation-map, a geometrical form of an X-ray beam to be radiated from the X-ray source to the X-ray detector;
wherein the situation-map is a positioning guide for the operator of the X-ray imaging system.

7. The X-ray imaging system according to claim 1, wherein the processing unit is configured to compute a simulation of at least one movement of the X-ray source and the X-ray detector; and
wherein the display unit is configured to display at least one resulting simulated spatial situation.

8. The X-ray imaging system according to claim 1, wherein the C-arm system is a portable system, wherein the C-arm is mounted to a support allowing movement of the C-arm, wherein the support is mounted to a moveable base.

9. A method for providing guiding information for operating an X-ray imaging system, comprising the following:
a) detecting object data of objects located between a moveable X-ray source and a moveable X-ray detector with a plurality of object-surface detecting sensors;
b) detecting current position of the X-ray source and the X-ray detector and the position of the sensors with a positioning detection arrangement;
c) computing a situation-map of the current spatial situation of a positional arrangement exclusively between the X-ray source and the X-ray detector based on the object data and the current position; and
d) displaying the situation-map on a display to a user operating the X-ray imaging system;
wherein the X-ray imaging system is a C-arm imaging system comprising a C-arm structure, wherein the X-ray source and the X-ray detector are mounted to opposing ends of a C-arm; wherein sensors are mounted to the C-arm structure in a distributed manner along an inner side of the arc; and wherein the positioning detection arrangement comprises angulation detectors for information about the movement of the C-arm;
wherein the situation-map is distinguishing at least between empty spaces and spaces occupied by rigid objects; and
wherein the situation-map comprises a representation of the X-ray source and the X-ray detector in relation to the positioning detection arrangement.

10. The method according to claim 9, wherein for d), a geometrical form of an X-ray beam to be radiated from the X-ray source to the X-ray detector is indicated in the situation-map as a positioning guide for the operator of the X-ray imaging system.

11. The method according to claim 9, wherein a simulation of at least one movement of the X-ray source and the X-ray detector is computed based on the computed situation map; and
wherein at least one resulting simulated spatial situation is displayed as a situation-simulation-map.

12. A non-transitory computer readable medium storing instructions, which when being executed by a processing unit, are adapted to perform the method according claim 9.

13. An X-ray imaging system, comprising:
a moveable X-ray source and a moveable X-ray detector;
a C-arm, the X-ray source and the X-ray detector being mounted to opposing ends of the C-arm structure;
a plurality of ultrasound sensors configured to detect object data of objects located between the X-ray source and the X-ray detector, the ultrasound sensors being sensors mounted to the C-arm structure in a distributed manner along an inner side of an arc of the C-arm;
angulation detectors configured to detect the current position of the X-ray source and the X-ray detector and the position of the ultrasound sensors;
at least one processor programmed to compute a a situation-map of the current spatial situation of a positional arrangement exclusively between the X-ray source and the X-ray detector based on the object data provided by the sensors and the current position, the situation-map comprising a representation of the X-ray source and the X-ray detector in relation to the angular detectors; and
a display configured to display the situation-map.

14. The X-ray imaging system according to claim 13, wherein the at least one processor is further programmed to compute empty spaces and spaces occupied by rigid objects of the situation-map.

15. The X-ray imaging system according to claim 14, wherein the angulation detectors are configured to provide information about the movement of the C-arm.

16. The X-ray imaging system according to claim 13, wherein the ultrasound sensors are configured to obtain surface data of a number of spatial segments; and
wherein the at least one processor is further programmed to combine the surface data of the spatial segments to form a topogram.

* * * * *